United States Patent [19]

Tomita et al.

[11] Patent Number: 4,810,808
[45] Date of Patent: Mar. 7, 1989

[54] PROCESS FOR PREPARING POLYGLYCIDYL COMPOUNDS

[75] Inventors: Haruo Tomita; Kazuya Yonezawa, both of Kobe, Japan

[73] Assignee: Kanegafuchi Kagaku Kogyo Kabushiki Kaisha, Osaka, Japan

[21] Appl. No.: 77,994

[22] Filed: Jul. 27, 1987

Related U.S. Application Data

[63] Continuation of Ser. No. 798,149, Nov. 15, 1985, abandoned, which is a continuation of Ser. No. 491,228, May 3, 1983, abandoned.

[30] Foreign Application Priority Data

May 14, 1982 [JP] Japan ................................. 57-82095

[51] Int. Cl.$^4$ .................. C07D 303/16; C07D 303/28
[52] U.S. Cl. ..................................... 549/515; 549/516; 549/517
[58] Field of Search ..................... 549/515, 516, 517

[56] References Cited

U.S. PATENT DOCUMENTS

| | | | |
|---|---|---|---|
| 2,772,296 | 11/1956 | Mueller | 549/515 |
| 3,336,342 | 8/1967 | Frank et al. | 549/556 |
| 3,372,142 | 3/1968 | Smith | 549/515 |
| 3,399,174 | 8/1968 | Bremmer | 549/515 |
| 4,130,549 | 12/1978 | Ueno et al. | 549/515 |
| 4,284,573 | 8/1981 | Arnett et al. | 549/517 |
| 4,373,073 | 2/1983 | Wojtech et al. | 549/517 |

FOREIGN PATENT DOCUMENTS 23622  2/1982  Japan .

OTHER PUBLICATIONS

Robert L. Merker et al., Jour. Org. Chem. (1961) vol. 26, pp. 5180–5182.
George W. Gokel et al., Jour. Chem. Education, vol. 55 (6) Jun. 1978, pp. 350–354.
CA: 94:209461m (1981).
Tanaka et al., J. Macromol. Sci.-Chem., vol. A1 (8), Dec. 1967, pp. 1469–1485.

Primary Examiner—Richard L. Raymond
Attorney, Agent, or Firm—Antonelli, Terry & Wands

[57] ABSTRACT

A process for preparing a polyglycidyl compound in which an aromatic hydroxycarboxylic acid having phenolic hydroxyl group is reacted with an epihalohydrin in the presence of a phase transfer catalyst and the dehydrohalogenation is then conducted by acting an aqueous alkali solution on the reaction mixture obtained in the first step.

13 Claims, No Drawings

PROCESS FOR PREPARING POLYGLYCIDYL COMPOUNDS

This application is a continuation of application Ser. No. 798,149, filed Nov. 15, 1985, now abandoned which was a continuation of application Ser. No. 491,228, filed May 3, 1983, now abandoned.

BACKGROUND OF THE INVENTION

The present invention relates to a process for preparing a polyglycidyl compound, and more particularly to a process for preparing a polyglycidyl compound having a high purity by the reaction of an aromatic hydroxycarboxylic acid and an epihalohydrin.

The term "aromatic hydroxycarboxylic acid" or "hydroxycarboxylic acid" as used herein means an aromatic carboxylic acid having a phenolic hydroxyl group in the molecule.

Polyglycidyl compounds derived from hydroxycarboxylic acids are useful as epoxy resins. However, since these polyglycidyl compounds have a glycidyloxycarbonyl and a glycidyloxy group and the ester linkage of the glycidyl ester moiety is subject to hydrolysis by an alkali, the production thereof by the reaction of hydroxycarboxylic acids and epihalohydrins is not easy.

It is an object of the present invention to provide a novel process for preparing a polyglycidyl compound from a hydroxycarboxylic acid.

A further object of the invention is to provide a process for easily preparing a polyglycidyl compound having a high purity in a high yield by the reaction of a hydroxycarboxylic acid and an epihalohydrin.

These and other objects of the present invention will become apparent from the description hereinafter.

SUMMARY OF THE INVENTION

In accordance with the present invention, there is provided a process for preparing a polyglycidyl compound which comprises reacting an aromatic hydroxycarboxylic acid having a phenolic hydroxyl group with an epihalohydrin in the presence of a phase transfer catalyst, and reacting the resulting reaction mixture with an aqueous solution of an alkali metal hydroxide.

DETAILED DESCRIPTION

In the present invention, aromatic hydroxycarboxylic acids which are aromatic carboxylic acid compounds having at least one phenolic hydroxyl group in the molecule, are employed as a starting material. For instance, o-, m- and p-hydroxybenzoic acids and hydroxycarboxylic acids derived from polynuclear aromatic compounds can be employed. The number of carboxyl groups and hydroxyl groups included in the molecule are not limited to one.

In the first step of the process of the present invention, a hydroxycarboxylic acid and an epihalohydrin are reacted in the presence of a phase transfer catalyst and in the substantial absence of water. The reaction may be carried out with or without employing a solvent such as toluene, benzene or chlorobenzene. In this stage, the addition reaction of the hydroxycarboxylic acid and the epihalohydrin takes place, and a compound having halohydrin ether and halohydrin ester moieties is produced. A part of the halohydrin ether moiety or the halohydrin ester moiety is converted into glycidyl ether or glycidyl ester miety by deydrohalogenation owing to excess epihalohydrin.

Epichlorohydrin, epibromohydrin and epiiodohydrin are employed as an epihalohydrin. The epihalohydrin is employed in an equimolar or excess amount based on the total of carboxyl group and hydroxyl group of the hydroxycarboxylic acid, especially in an amount of 3 to 10 times the molar amount of carboxyl and hydroxyl groups of the hydroxycarboxylic acid.

The reaction in the first step is carried out at a temperature of 50° to 110° C., preferably 90° to 100° C. The reaction time varies depending on the reaction temperature and the kind of the hydroxycarboxylic acid used. For instance, in case of carrying out the reaction at a temperature of 90° to 100° C., the reaction time within the range of 30 minutes to 2 hours is sufficient.

The presence of the phase transfer catalyst is essential for the addition reaction. If the phase transfer catalyst is not present, the reaction scarcely proceed. The phase transfer catalyst is employed in an amount of 0.01 to 100% by mole, preferably 1 to 10% by mole, based on the hydroxycarboxylic acid. Phase transfer catalysts generally known are usable in the present invention. Representative examples of the phase transfer catalysts are, for instance, quaternary ammonium salts such as tetrabutylammonium bromide, trioctylmethylammonium chloride, benzyltriethylammonium chloride and benzyltrimethylammonium chloride, quaternary phosphonium salts such as tetraphenylphosphonium chloride and triphenylmethylphosphonium chloride, and quaternary arsonium salts.

In the second step of the process of the present invention, dehydrohalogenation of the halohydrin ether and halohydrin ester moieties of the reaction product obtained in the first step is conducted by adding an aqueous solution of an alkali metal hydroxide to the reaction mixture obtained in the first step or the reaction mixture from which the unreacted epihalohydrin is removed by distilling away, whereby the desired polyglycidyl compound having glycidyloxycarbonyl group and glycidyloxy group is produced. The reaction is conducted by vigorously agitating the reaction mixture obtained in the first step and an aqueous alkali solution. The reaction temperature is selected so that the dehydrohalogenation reaction sufficiently proceeds and moreover the hydrolysis of the ester linkage is prevented. Usually, the reaction is conducted at a temperature of 20° to 30° C. The reaction time required in completing the dehydrohalogenation varies depending on the reaction temperature. Usually, the reaction is conducted for 20 minutes to 2 hours.

Sodium hydroxide and potassium hydroxide are usually employed as alkali metal hydroxides. The amount of the alkali metal hydroxide is not less than 0.5 time, preferably from 1.0 to 1.5 times, the molar amount of the total of carboxyl group and hydroxyl group of the hydroxycarboxylic acid used as a starting material. The concentration of the aqueous solution of an alkali metal hydroxide is selected from 1 to 50% by weight, preferably 5 to 20% by weight.

Upon conducting the dehydrohalogenation reaction, the phase transfer catalyst may be additionally added to the reaction system, since the reaction is accelerated and is copleted in a short period of time at a low temperature, whereby the loss of the product due to hydrolysis of the formed glycidyl ester moiety can be decreased.

After the completion of the dehydrohalogenation reaction, the reaction mixture separates into two layers.

The end product, namely the polyglycidyl compound, is recovered by removing the aqueous layer from the reaction mixture and washing the organic layer with water several times, and if necessary, further distilling away the unreacted epihalohydrin under reduced pressure.

According to the process of the present invention, polyglycidyl compounds having a high epoxy content can be easily obtained from hydroxycarboxylic acids in high yields. For instance, in case of employing p-hydroxybenzoic acid as a starting material, almost pure glycidyl p-glycidyloxybenzoate is obtained in high yields.

As mentioned before, the feature of the process of the present invention resides in using a phase transfer catalyst. The use of the phase transfer catalyst has the advantage that the addition reaction of the hydroxycarboxylic acid and the epihalohydrin in the first step is promptly started and completed. The process of the invention using the phase transfer catalyst also has the advantage that the loss of the product due to hydrolysis of the glycidyl ester moiety is scarcely seen because the dehydrohalogenation reaction of the halohydrin ether moiety and the halohydrin ester moiety can be completed in a short period of time at a low temperature. Therefore, the process of the present invention does not require a troublesome procedure as conducted usually in a conventional process for preparing glycidyl esters such that the addition of an aqueous solution of an alkali metal hydroxide is conducted under an azeotropic dehydration condition.

The process of the present invention is more specifically described and explained by means of the following Examples. It is to be understood that the present invention is not limited to the Examples, and various changes and modifications may be made in the invention without departing from the spirit and scope thereof.

EXAMPLE 1

A mixture of 1.38 g. (10 millimoles) of p-hydroxybenzoic acid, 11 g. (120 millimoles) of epichlorohydrin and 0.23 g. (1 millimole) of benzyltriethylammonium chloride was agitated at 100° C. for 30 minutes. After cooling the reaction mixture to 30° C., 4.0 g. of a 20% by weight aqueous solution of sodium hydroxide was added to the reaction mixture, and the mixture was agitated at 30° C. for 30 minutes. The reaction mixture was allowed to stand, and after removing an aqueous layer, the remaining layer was washed twice with water. The unreacted epichlorohydrin was distilled away at 110° C. under reduced pressure to give 2.48 g. of a colorless transparent liquid (yield: 99%). The liquid crystallized at room temperature. The epoxy equivalent of the product measured by a hydrochloric acid-dioxane method was 140 (theoretical value for glycidyl p-glycidyloxybenzoate: 125).

The product was recrystallized from methanol to give colorless plate crystals having a melting point of 55° to 56° C. (value in literature for glycidyl p-glycidyloxybenzoate: 56° to 58° C.). In infrared absorption spectrum, no absorptions for carboxyl group and phenolic hydroxyl group were observed, and there were observedd absorptions for terminal epoxy group at 3,050 and 910 cm.$^{-1}$ and absorption for ester at 1,715 to 1,720 cm.$^{-1}$

EXAMPLE 2

A mixture of 1.38 g. (10 millimoles) of p-hydroxybenzoic acid, 11 g. (120 millimoles) of epichlorohydrin and 0.23 g. (1 millimole) of benzyltriethylammonium chloride was agitated at 100° C. for 40 minutes. The reaction mixture was cooled to 28° C., and thereto was added 2.0 g. of a 20% by weight aqueous solution of sodium hydroxide and the mixture was vigorously agitated at 28° C. for 20 minutes. After allowing to stand and removing an aqueous layer, the reaction mixture was washed twice with water. The unreacted epichlorohydrin was distilled away at 100° C. and 3 mmHg to give 2.69 g. of a colorless transparent liquid. This liquid did not crystallize at room temperature. The epoxy equivalent of the product was 147.

EXAMPLE 3

A mixture of 1.38 g. (10 millimoles) of p-hydroxybenzoic acid, 11 g. (120 millimoles) of epichlorohydrin and 0.23 g. (1 millimole) of benzyltriethylammonium chloride was agitated at 100° C. for 40 minutes. The unreacted epichlorohydrin was distilled away from the reaction mixture at 100° C. and 3 mmHg to give 2.76 g. of a colorless liquid. In infrared spectrum of this product, there were observed an absorption for hydroxyl group of chlorohydrin at 3,450 cm.$^{-1}$, an absorption for ester at 1,710 cm.$^{-1}$ and absorptions for terminal epoxy group at 3,050 and 910 cm.$^{-1}$ The epoxy equivalent of the product measured by a hydrochloric acid-dioxane method was 220.

The product was then dissolved in 30 ml. of methylene chloride, and thereto was added 4.0 g. of a 20% by weight aqueous solution of sodium hydroxide. The mixture was vigorously agitated at 30° C. for 30 minutes. After allowing the reaction mixture to stand and removing an aqueous layer, methylene chloride was distilled away from the organic layer at 100° C. and 3 mmHg to give 2.40 g. of a colorless transparent liquid. The liquid crystallized at room temperature. The infrared absorption spectrum of this product was identical with that obtained in Example 1. The epoxy equivalent of the product was 143.

EXAMPLE 4

A mixture of 1.38 g. (10 millimoles) of o-hydroxybenzoic acid, 11 g. (120 millimoles) of epichlorohydrin and 0.23 g. (1 millimole) of benzyltriethylammonium chloride was agitated at 100° C. for 2 hours. After cooling the reaction mixture to 30° C., 4.0 g. of a 20% by weight aqueous solution was added to the reaction mixture, and the reaction was conducted at 30° C. for 30 minutes with agitation. After allowing to stand and removing an aqueous layer, the reaction mixture was washed twice with water. The unreacted epichlorohydrin was then distilled away at 110° C. under reduced pressure to give 2.49 g. of a colorless liquid (yield: 99.5%). The epoxy equivalent of the product was 200.

In addition to the ingredients used in the Examples, other ingredients can be used in the Examples as set forth in the specification to obtain substantially the same results.

What we claim is:

1. A process for preparing a polyglycidyl compound which comprises reacting an aromatic hydroxycarboxylic acid having a phenolic hydroxyl group with an epihalohydrin in the presence of a phase transfer catalyst selected from the group consisting of a quaternary ammonium salt, a quaternary phosphonium salt and a quaternary arsonium salt in the substantial absence of water, and reacting the resulting reaction mixture with a 5 to 20% by weight aqueous solution of an alkali metal hydroxide at a temperature of 20° to 30° C.; the epihalohydrin being employed in an amount of 3 to 10 times the molar amount of carboxyl and hydroxyl groups of the hydroxycarboxylic acid and the phase transfer catalyst being present in an amount of 1 to 10% by mole, based on the hydroxycarboxylic acid.

2. The process of claim 1, wherein the phase transfer catalyst is a quaternary ammonium salt.

3. The process of claim 1, wherein the aromatic hydroxycarboxylic acid is hydroxybenzoic acid.

4. The process of claim 1, wherein the phase transfer catalyst is selected from the group consisting of tetrabutylammonium bromide, trioctyl methyl ammonium chloride, benzyltriethyl ammonium chloride, benzyltrimethylammonium chloride, tetraphenylphosphonium chloride and triphenylmethylphosphonium chloride.

5. The process of claim 1, wherein the reaction of the resulting reaction mixture with the aqueous solution of an alkali metal hydroxide is conducted for 20 minutes to 2 hours.

6. The process of claim 1, wherein the amount of alkali metal hydroxide is from 0.5 to 1.5 times the molar amount of the total of the carboxyl group and hydroxyl group content of the hydroxycarboxylic acid reacted with the epihalohydrin.

7. The process of claim 6, wherein the reaction of the resulting reaction mixture with the aqueous solution of an alkali metal hydroxide is conducted for 20 minutes to 2 hours.

8. The process of claim 1, wherein the epihalohydrin is epichlorohydrin, epibromohydrin or epiiodohydrin.

9. The process of claim 1, wherein the hydroxycarboxylic acid and the epihalohydrin are reacted in the presence of the phase transfer catalyst at a temperature of 50° to 110° C.

10. The process of claim 1, wherein the hydroxycarboxylic acid and the epihalohydrin are reacted in the presence of the phase transfer catalyst at a temperature of 90° to 100° C.

11. The process of claim 9, wherein the phase transfer catalyst is selected from the group consisting of tetrabutylammonium bromide, triocyl methyl ammonium chloride, benzyltriethyl ammonium chloride, benzyltrimethylammonium chloride, tetraphenylphosphonium chloride and triphenylmethylphosphonium chloride.

12. The process of claim 1, wherein upon completion of reaction of the resulting reaction mixture with the alkali metal hydroxide, the obtained reaction mixture is allowed to separate into two layers, the polyglycidyl compound product being recovered by removing an aqueous layer from the two layers, the remaining organic layer being washed with water and thereafter excess epichlorohydrin being distilled away from the organic layer.

13. A process for preparing a polyglycidyl compound which comprises reacting an aromatic hydroxycarboxylic acid having a phenolic hydroxyl group with an epihalohydrin in the presence of a phase transfer catalyst selected from the group consisting of a quaternary ammonium salt, a quaternary phosphonium salt and a quaternary arsonium salt in the substantial absence of water, distilling away excess epihalohydrin from the resulting reaction mixture, and reacting the resultant reaction mixture with a 5 to 20% by weight aqueous solution of an alkali metal hydroxide at a temperature of 20° to 30° C.; the epihalohydrin being employed in an amount of 3 to 10 times the molar amount of carboxyl and hydroxyl groups of the hydroxycarboxylic acid and the phase transfer catalyst being present in an amount of 1 to 10% by mole, based on the hydroxycarboxylic acid; the resultant reaction mixture being dissolved in methylene chloride prior to reacting with the alkaline metal hydroxide.

* * * * *